United States Patent [19]
Gray et al.

[11] 3,947,375
[45] Mar. 30, 1976

[54] LIQUID CRYSTAL MATERIALS AND DEVICES

[75] Inventors: George William Gray, Cottingham; Kenneth John Harrison, Hull, both of England

[73] Assignee: Secretary of State for Defence in Her Britannic Majesty's Government of United Kingdom of Great Britain and Northern Ireland, London, England

[22] Filed: Nov. 6, 1973

[21] Appl. No.: 413,247

[30] Foreign Application Priority Data
Nov. 9, 1972 United Kingdom............... 51698/72
July 16, 1973 United Kingdom............... 33709/73

[52] U.S. Cl. ............ 252/299; 23/230 LC; 252/408; 260/465 R; 260/465 D; 260/465 G; 260/465 F; 260/465 K; 260/473 R; 260/611 A; 260/645; 260/649 DP; 350/160 LC; 428/1
[51] Int. Cl.² ............... C09K 3/34; C07C 121/64; C07C 121/66; C07C 121/70; G02F 1/01; G02F 1/03; G02F 1/13; G02B 5/23
[58] Field of Search .................. 252/299, 408 LC, ; 350/160 LC; 260/465 F, 645, 465 D, 465 R, 465 G, 473 R, 649 DP, 611 A, 465 K; 23/230 LC; 428/1

[56] References Cited
UNITED STATES PATENTS

| | | | |
|---|---|---|---|
| 2,682,562 | 6/1954 | Wender et al. .................... | 260/645 |
| 3,322,485 | 5/1967 | Williams ............................ | 252/299 |
| 3,636,168 | 1/1972 | Josephson........................ | 260/649 DP |
| 3,666,948 | 5/1972 | Mechlowitz et al. ........ | 252/408 LC |
| 3,691,755 | 9/1972 | Girard............................... | 252/299 |
| 3,697,150 | 10/1972 | Wysochi .......................... | 252/299 |
| 3,767,289 | 10/1973 | Aviram et al................ | 252/408 LC |
| 3,773,747 | 11/1973 | Steinstrasser................ | 252/408 LC |
| 3,795,436 | 3/1974 | Doller et al......................... | 252/299 |
| 3,796,479 | 3/1974 | Helfrich et al..................... | 252/299 |

FOREIGN PATENTS OR APPLICATIONS

| | | | |
|---|---|---|---|
| 1,227,616 | 4/1971 | United Kingdom................ | 252/299 |
| 2,306,739 | 8/1973 | Germany ............................ | 252/299 |

OTHER PUBLICATIONS

Gray, G. W. et al.; Electronics Letters, Vol. 9, No. 6, pp. 130–131 (Mar. 1973).
Gray, G. W. et al.; Electronics Letters, Vol. 9, No. 26, pp. 616–617 (Dec. 1973).
Gray, G. W.; "Molecular Structure and the Properties of Liquid Crystals," Academic Press, N.Y. (1962).
"Umwandlungstemperaturen Kristalliner Flussigkeiten," Kast, Landolt–Bornstein, Vol. 2, Part II, 6th Ed. pp. 266–267, 292, 293, 296–299 (1960).
C. A., Vol. 64, p. 12525c (1966), "Polarography, . . . of P-Nitrobiphenyls."
Usol'Tseva et al., Russian Chemical Reviews, Vol. 32, No. 9, pp. 495–509, (Sept. 1963).
Rondeau, R. E. et al., J. Amer. Chem. Soc., Vol. 94, No. 4, pp. 1096–1102, (Feb. 1972).
Schadt, M., J. Chem. Phys., Vol. 56, No. 4, pp. 1494–1497, (Feb. 1972).

*Primary Examiner*—Benjamin R. Padgett
*Assistant Examiner*—T. S. Gron
*Attorney, Agent, or Firm*—Stevens, Davis, Miller & Mosher

[57] ABSTRACT

A novel liquid crystal material contains a compound having a molecular structure such that the material exhibits a liquid crystal phase, the molecular structure of the compound being

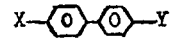

or an orthosubstituted derivative thereof, where X and Y are different parasubstituents of the kind which promote liquid crystal behaviour, where the para substituent is a group selected from the following list; an alkyl group, an acyloxy group, an unsaturated group or an alkoxy group having more than one carbon atom; and where the para-substituent Y is a group selected from the following list; a cyano group, a nitro group, a group which includes a terminal cyano group, a group which includes a terminal nitro group and an acyloxy group. The material may be the said compound or it may be a multi-component solution or mixture containing it. The liquid crystal material may be nematic, smectic or cholesteric depending on the selection of the substituents X and Y. A device such as a twisted nematic effect device, incorporating the material may be operated at low temperatures. The material does not suffer from significant chemical and/or photochemical decomposition when used in a liquid crystal device.

44 Claims, 3 Drawing Figures

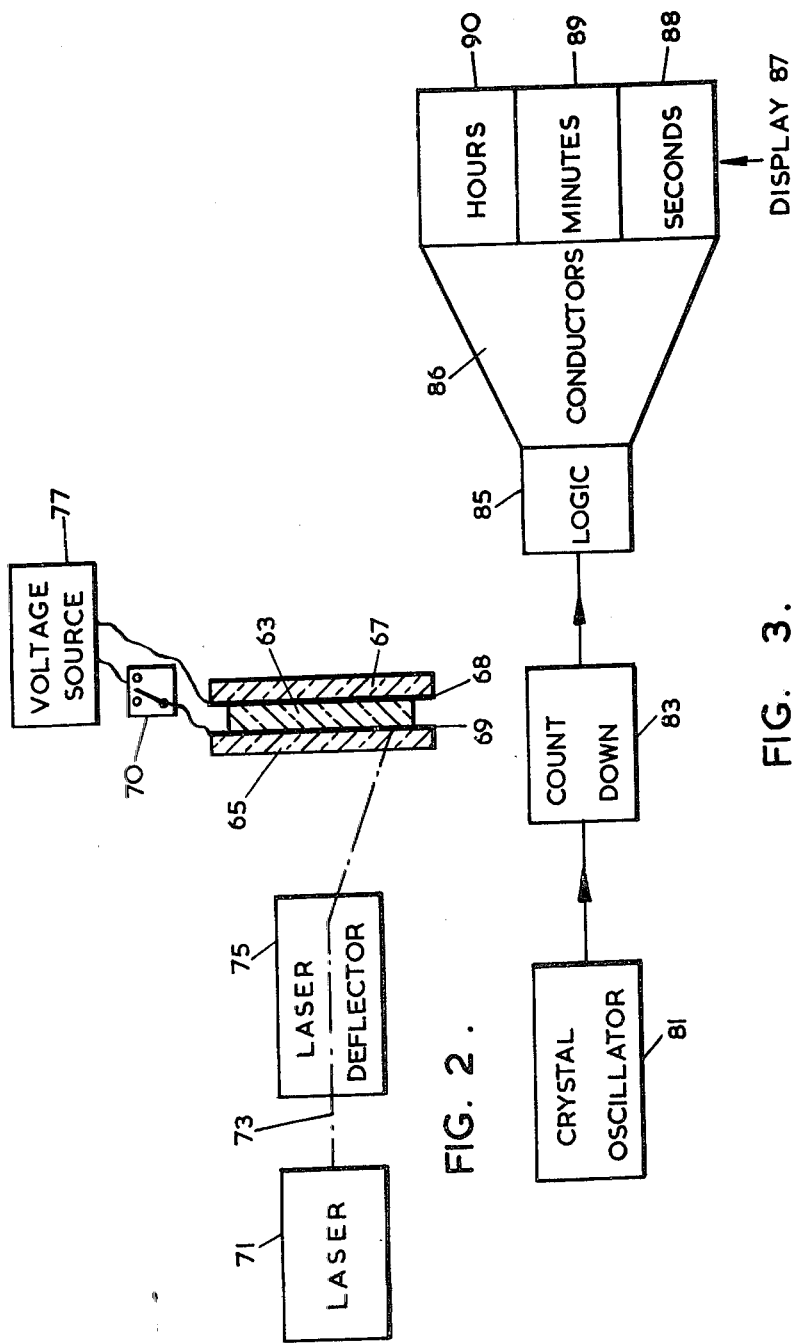

LIQUID CRYSTAL MATERIALS AND DEVICES

The present invention relates to liquid crystal materials and devices.

In the field of displays there is a requirement for devices having a low power consumption. Devices made from liquid crystal materials have been shown to satisfy this requirement because they have a very large electrical resistance, and at the present time a considerable amount of interest is being shown in such devices for this reason.

There are many known liquid crystal materials; some have been known for many years. Liquid crystal materials are organic materials which exhibit liquid crystal phase in which the molecules are arranged over limited spatial ranges in an ordered structure.

There are three known kinds of liquid crystal phase. One is known as a smectic mesophase in which the ordering of the molecules is of a lamellar kind. Another is known as a nematic mesophase in which a statistical ordering of the molecules exists parallel to the long axes of the molecules. The third is known as a cholesteric mesophase, in which the ordering of the molecules is of a helical kind.

Liquid crystal materials consist of compounds having a molecular structure which is elongated. For the liquid crystal compounds which have hitherto been used in devices the structure can be generalised and represented as follows:

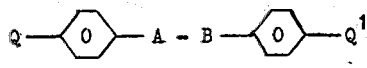

where Q and $Q^1$ are terminal groups and A and B are linkage groups.

Except in the case of certain esters where the unit A–B includes the group CO.O the unit A–B generally includes a double or triple bond. For example the Schiff's bases which are widely used in commercial liquid crystal devices, such as para-methoxy-benzylidene-butylaniline (MBBA) or para-ethoxy-benzylidene-butylaniline (EBBA) are compounds containing the unit $C = N$.

The presence of a double or triple bond in the unit A–B leads to a chemical and/or photochemical instability of the material and is therefore undesirable for this reason. For example, Schiff's bases are readily hydrolysed, even by traces of water, yielding potentially toxic amines.

It has hitherto been supposed that the double or triple bond in the unit A–B is desirable to confer rigidity on the molecule and to provide a reasonably high liquid crystal to isotropic liquid transition temperature together with a reasonably low crystalline solid to liquid crystal transition temperature.

It is an object of the present invention to reduce the instability of a liquid crystal material having the generalised formula

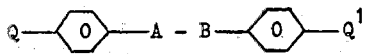

in the unit A – B.

It is also an object of the present invention to provide a liquid crystal material which is useful in device applications.

It is also an object of the present invention to provide a liquid crystal material which exhibits a nematic liquid crystal phase and which is useful in device applications.

It is also an object of the present invention to provide a liquid material which exhibits a cholesteric liquid crystal phase and which is useful in device applications.

It is also an object of the present invention to provide a liquid crystal material which exhibits a smectic liquid crystal phase which is useful in device applications.

It is also an object of the present invention to provide a liquid crystal device wherein the liquid crystal material exhibits a liquid crystal phase at ambient temperatures.

According to the present invention a liquid crystal material consists of or contains a compound having a molecular structure such that the material exhibits a liquid crystal phase, the molecular structure of the compound being

or a simple ortho-substituted derivative thereof or a derivative thereof in which a simple bridging group is contained between two of the ortho-positions thereof, where X and Y are different para-substituents of the kind which promote liquid crystal behaviour, the para-substituent X being a group selected from the following list: an alkoxy group having more than one carbon atom; an alkyl group; an acyloxy group; and an alkenyl group; and the para-substituent Y being selected from the following list: a cyano group; a nitro group; an acyloxy group; a benzene ring substituted in the para-position by a cyano group or by a nitro group or by an acyloxy group; and a plurality of directly para-linked benzene rings in which the end ring remote from the substituent X is substituted in the para-position by a cyano group or by a nitro group or by an acyloxy group.

Certain biphenyl compounds having a structure

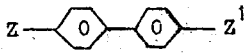

have been known previously to exhibit liquid crystal phases. However in all of these known compounds the para-substituents Z and $Z^1$ have been of such a kind that these known compounds have exhibited their crystalline solid to liquid crystal transitions at very high temperatures; as a consequence these known compounds have had no usefulness in known device applications.

By introducing the para-substituents X and Y in accordance with the invention to produce the said liquid crystal material defined above reasonably low crystalline solid to liquid crystal and reasonably high liquid crystal to isotropic liquid transition temperatures can be obtained such that the material according to the invention can be used in known device applications. Furthermore because the material according to the invention does not contain a double or triple bond in the position corresponding to the unit A – B of the generalised liquid crystal molecular structure given above, the chemical and photochemical stability of the said material is improved.

The material according to the invention may consist of the said compound. Alternatively, the material may be a multi-component mixture or solution of which at least one of the components is the said compound.

The liquid crystal phase (mesophase) exhibited by the material according to the invention may be nematic, smectic or cholesteric. In order for the phase to be cholesteric, one of the para-substituents X, Y of the said compound must contain an asymmetric centre, such as that which may exist in a branched carbon chain, so that the compound is optically active.

By an 'ortho-substituted' derivative of the structure

is meant a derivative in which any one or more of the remaining positions on any one (or more) of the benzene rings of the structure, including the benzene ring(s) which may be contained within the para-substituent Y, is(are) substituted.

By the 'ortho-positions' is meant any of the remaining positions on any one or more of the benzene rings of the structure, including the benzene rings which may be contained within the para-substituent Y.

By a 'simple ortho-substituted derivative' is meant an orthosubstituted derivative in which the ortho-substituent(s) does(do) not disrupt the liquid crystalline behaviour of the material containing it(them). Examples of suitable ortho-substituents are a methyl group and a halogen atom.

Similarly, by a 'simple bridging group' is meant a bridging group which does not disrupt the liquid crystalline behaviour of the material containing it. Examples of suitable bridging groups are as follows:

the group $>CH_2$ to form a fluorene;

the group $>C=O$ to form a fluorenone;

and the group

to form a phenanthrene

According to another aspect of the present invention a liquid crystal device includes means for containing a region of liquid crystal material, a region of liquid crystal material contained in the containing means, wherein the liquid crystal material is the material according to the invention defined above, and means for applying an external stimulus to the material to alter the molecular arrangement in the liquid crystal material.

The means for applying an external stimulus may for example be means for applying an electric field to the region, means for applying a magnetic field to the region or means for applying a temperature change to the region.

The change in molecular arrangement produced by the external stimulus may be used to affect the transmission of electromagnetic radiation at any wavelength of the interest through the material, for example, by changing the transmissivity of the material or by changing the optical activity of the material, if it is optically active.

According to another aspect of the invention, an electro-optic liquid crystal device includes two adjacent glass plates at least one of which is optically transparent, a layer of liquid crystal material contained in the space between the plates wherein the liquid crystal material is the material according to the invention defined above, and deposited on the inner facing surfaces of the plates, a film of conducting material to allow an electric field to be applied across the layer. The electro-optic device may for example be a display device used, for instance, in an instrument such as a time watch or clock.

Embodiments of the present invention will be described by way of example with reference to the accompanying drawings, in which:

FIG. 2 is a schematic diagram of a liquid crystal information storage device.

FIG. 3 is a schematic diagram of a time clock or watch incorporating a liquid crystal display embodying the present invention.

Figure 1:
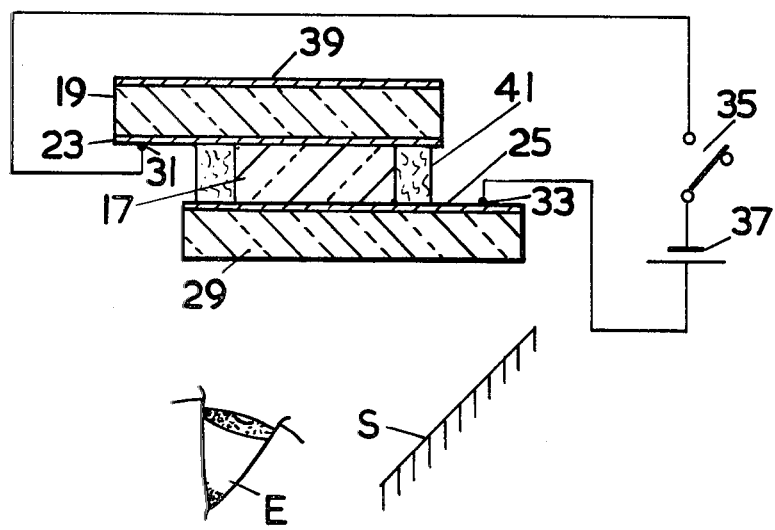
FIG. 1 is a cross-sectional plan view (partly in circuit form) of an electro-optic device embodying the invention.

It has been discovered in connection with the present invention that materials containing compounds having the formula

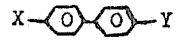

defined above may be synthesised and exhibit at least one liquid crystal phase (mesophase). The phase(s) may be cholesteric or nematic and/or smectic. The phase(s) may be exhibited at relatively low temperatures; this is a very desirable property of materials to be used in liquid crystal device applications.

For example some compounds exhibiting a nematic liquid crystal phase are listed in Table 1 together with their crystal to nematic liquid crystal and nematic liquid crystal to isotropic liquid transition temperatures. Each compound is of the form

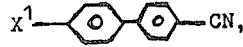

where $X^1$ represents an n-alkyl or an n-alkoxy group and is represented in Table 1 in an abbreviated form by its particular group $X^1$.

TABLE 1

Transition temperatures for compounds $X^1$—⟨O⟩—⟨O⟩—CN

| $X^1$ | Crystal to Nematic transition temperature (°C) | Nematic to Isotropic transition temperature (°C) |
|---|---|---|
| n—$C_5H_{11}$ | 22.5 | 35 |
| n—$C_6H_{13}$ | 13.5 | 27 |
| n—$C_7H_{15}$ | 28.5 | 42 |
| n—$C_5H_{11}O$ | 48 | 67.5 |
| n—$C_6H_{13}O$ | 58 | 76.5 |
| n—$C_7H_{15}O$ | 53.5 | 75 |

For example also some two-component mixtures exhibiting a nematic liquid crystal phase are listed in Table 2 together with their crystal to nematic liquid crystal and nematic liquid crystal to isotropic liquid transition temperatures. Each constituent compound in each mixture is of the form

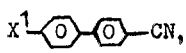

where $X^1$ represents an n-alkyl group or an n-alkoxy group and is represented in Table 2 in an abbreviated form by its particular group $X^1$. A suitable mole percentage for each constituent compound in each mixture is also listed.

TABLE 2

Transition temperatures for binary mixtures of compounds 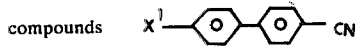

| | Mole % | Crystal to Nematic transition temperature (°C) | Nematic to Isotropic transition temperature (°C) |
|---|---|---|---|
| Mixture 1 | | | |
| n—$C_7H_{15}$ | 48.5 | 0.5 | 40 |
| n—$C_8H_{17}$ | 51.5 | | |
| Mixture 2 | | | |
| n—$C_5H_{11}O$ | 55 | 21 | 70.5 |
| n—$C_7H_{15}O$ | 45 | | |
| Mixture 3 | | | |
| n—$C_5H_{11}$ | 83.5 | 15 | 42 |
| n—$C_6H_{13}O$ | 16.5 | | |

For example also some mixtures exhibiting a cholesteric liquid crystal phase are listed in Table 3, together with their crystal to cholesteric liquid crystal and cholesteric liquid crystal to isotropic liquid transition temperatures. Each constituent compound in each mixture is of the form

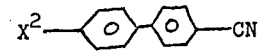

where $X^2$ represents an alkyl or alkoxy group which has either a normal or branched chain of carbon atoms; each constituent compound is represented in an abbreviated form by its particular group $X^2$. A suitable mole percentage for each constituent compound is also listed.

TABLE 3

| $X^2$ | Mole % | Crystal to cholesteric transition temperature (°C) | Cholesteric to isotropic transition temperature (°C) |
|---|---|---|---|
| Mixture 4 | | | |
| n—$C_5H_{11}O$ | 33 | | |
| n—$C_7H_{15}O$ | 27 | 12.5 | 48 |
| $CH_3.CH_2.C^*H.CH_2O$ $\mid$ $CH_3$ | 40 | | |
| Mixture 5 | | | |
| n—$C_5H_{11}O$ | 21 | | |
| n—$C_7H_{15}O$ | 17 | 11.5 | 53 |
| n—$C_8H_{17}O$ | 22 | | |
| $CH_3.CH_2.C^*H.CH_2O$ $\mid$ $CH_3$ | 40 | | |

In Mixtures 4 and 5 the asterisk (*) represents an asymmetric centre which causes the compound containing it to be optically active. For example also the compound

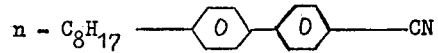

exhibits a smectic liquid crystal phase from 21°C to 32.5°C and a nematic liquid crystal phase from 32.5°C to 40°C.

Examples of methods of preparing compounds

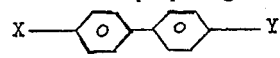

and ortho substituted derivatives thereof, as defined above will now be described.

EXAMPLE 1

Preparation of 4'-alkyl-4-cyanobiphenyls by the following route:

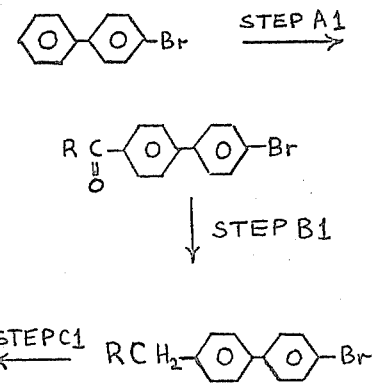

where R is an alkyl group, for example an n-alkyl group.

STEP A1: The production of 4'-m-acyl-4-bromobiphenyl (by FriedelCraft Acylation).

One example of a way of carrying out this step is as follows:

To commercially available 4-bromobiphenyl (0.08 mole) and anhydrous aluminium trichloride (0.1 mole) dissolved in dry "AnalaR" nitrobenzene (85 ml), the appropriate n-acyl chloride (0.1 mole) is added in drops, the temperature being maintained below 20°C. The solution is stirred for about 18 hours at room temperature and poured onto a mixture of ice, water and concentrated hydrochloric acid. The mixture is then stirred for about 0.5 hour, and the nitrobenzene layer separated. The nitrobenzene is removed by steam distillation, and the residue is crystallised from absolute ethanol to constant melting point. STEP B1: The production of 4'-n-alkyl-4-bromobiphenyl (by Huang Min lon Reduction).

One example of a way of carrying out this step is as follows:

To the appropriate bromoketone(0.037 mole) dissolved in a mixture of dry diethylene glycol (60 ml) by warming, a solution of (90%) hydrazine hydrate (0.08 mole) in dry diethylene glycol (20 ml) is added. Potassium hydroxide (0.09 mole) is added to the warm solution, and after heating at about 100°C until most of the solid is dissolved, the reaction mixture is heated under reflux for about 1 hour. The temperature is raised to about 180°C by distillation and maintained at about 180°C for 4 hours. On cooling, the reaction mixture is shaken with benzene and the extract is dried. The solvent is removed and the residue is crystallised from absolute ethanol to constant melting point.

STEP C1: The production of 4'-n-alkyl-4-cyanobiphenyl.

One example of a way of carrying out this step is as follows:

A mixture of the 4'-n-alkyl-4-bromobiphenyl (0.021 mole) prepared by steps A and B and cuprous cyanide (0.031 mole) in dry dimethylformamide (75 ml) is heated under reflux for about 12 hours. On cooling the reaction mixture is poured onto a stirred mixture of ferric chloride, concentrated hydrochloric acid and water. After heating at about 60°–70°C for 20 minutes the mixture is shaken with chloroform and the extract washed with 5N hydrochloric acid, water, 10% aqueous sodium hydroxide, water and then dried. The solvent is removed and the residue purified by column chromatography on silicic acid, followed by crystallisation from light petroleum (boiling point 40°–60°C) at −78°C to constant melting point. Finally the product is distilled under vacuum (0.5mm Hg) at about 140°–150°C.

EXAMPLE 2

Preparation of 4-alkoxy-4'-cyanobiphenyls by the following route:

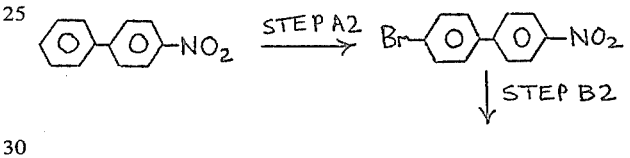

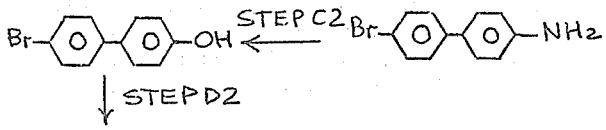

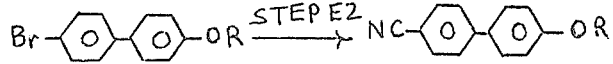

where R is an alkyl group, for example an n-alkyl group.

STEP A2: The production of 4-bromo-4'-nitrobiphenyl.

One example of a way of carrying out this step is as follows:

Commercially available 4-nitrobiphenyl is brominated by the method of LeFevre and Turner (as described in J Chem Soc 1926), p.2045) to give 4'-bromo-4-nitrobiphenyl.

STEP B2: The production of 4-bromo-4'-aminobiphenyl.

One example of a way of carrying out this step is as follows:

Reduction of the nitro-compound produced by Step A2 (81g) is achieved by stirring at 100°C for about 12 hours with a mixture of iron pin dust (58g), ethanol (500 ml; 90%) and concentrated hydrochloric acid (29ml). sodium carbonate (22g) is added and stirring is continued for 30 minutes whereupon a slight excess of dilute aqueous ammonia is added. On cooling, the amine formed is extracted into ether. The combined ether/alcohol extract of the amine is evaporated to remove the ether, and the residue is poured into water. The amine is precipitated, filtered off and dried.

STEP C2: The production of 4-Bromo-4'-hydroxybiphenyl.

One example of a way of carrying out this step is as follows;

4'-Amino-4-bromobiphenyl (60g) produced by step B2 is dissolved in aqueous 95% acetic acid (360ml) at 90°C, and to the solution vigorously stirred is added rapidly 40% w/w sulphuric acid (360ml) preheated to 90°C. Stirring and rapid cooling to 0°C gives the finely divided amine sulphate, which is diazotised at 0°C (± 1°C) by the slow addition of aqueous sodium nitrite (41.6g) in water (100ml). The excess of sodium nitrite is then destroyed with urea. 95% Acetic acid (400ml) is then added to effect solution of the diazonium salt. The ice-cold solution of the diazonium sulphate is run immediately into a vigorously stirred and boiling solution of 40. w/w sulphuric acid (200ml). The solution is added slowly at first, until suspended particles are visible in the mixture, after which the rate of addition is increased. The time required for the addition is about 30 minutes. The solution is then heated under reflux for about 15 minutes and cooled; dilution with an equal volume of water gives a solid which is digested with hot N-sodium hydroxide solution (300ml). After removal of insoluble material by filtration, the filtrate is acidified to give colourless 4-bromo-4'-hydroxybiphenyl.

STEP D2: The production of 4'-n-alkoxy-4-bromobiphenyls.

One example of a way of carrying out this step is as follows:

To a mixture of 4-bromo-4'-hydroxybiphenyl produced by step C2 (0.033 mole) and anhydrous potassium carbonate (0.132mole) in cyclohexanone (70 ml), the appropriate n-alkyl bromide (0.053 mole) is added and the stirred mixture heated under reflux for about 4 hours. On cooling, the reaction mixture is filtered, and the solvent is removed from the filtrate. The residue is crystallised from a mixture of benzene and light petroleum (boiling point 40°–60°C) to constant melting point.

STEP E2: The production of 4'-n-alkoxy-4-cyanobiphenyls.

One example of a way of carrying out this step is as follows:

A mixture of 4'-n-alkoxy-4-bromobiphenyl (0.024 mole) produced by step D2 and cuprous cyanide (0.036 mole) in dry dimethylformamide (100ml) is heated under reflux for about 12 hours. On cooling, the reaction mixture is poured onto a mixture of ferric chloride, concentrated hydrochloric acid and water. After heating at 60°–70°C for about 20 minutes the mixture is shaken with chloroform and the extract washed with 5N hydrochloric acid, water, 20% aqueous sodium hydroxide, water and then dried. The solvent is removed and the residue purified by column chromatography on silicic acid, followed by crystallisation from light petroleum (boiling point 40°–60°C) at −78°C to constant melting point. Finally the product is distilled under vacuum (0.5mm Hg) at about 140°C.

EXAMPLE 3

Preparation of 4'-alkyl-4-nitrobiphenyls by the following route;

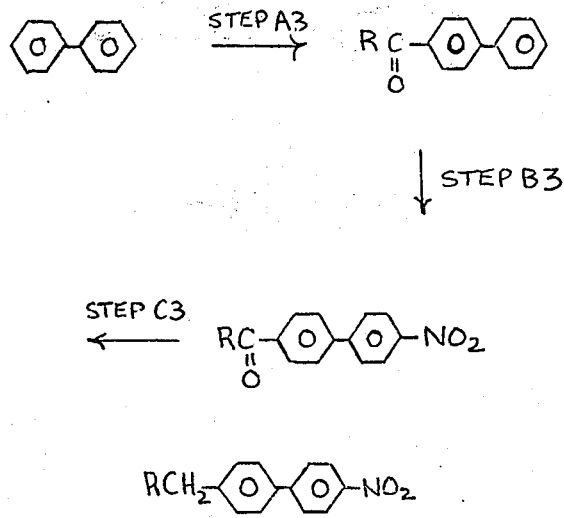

where R is an alkyl group, for example an n-alkyl group.

STEP A3: Production of a 4-acylbiphenyl:

One example of a way of carrying out this step is as follows:

Commercially available biphenyl is converted by Friedel-Crafts acylation to the appropriate 4-acyl-biphenyl.

STEP B3: Production of 4'-acyl-4-nitro-biphenyl:

One example of a way of carrying out this step is as follows:

Nitration of the 4-acylbiphenyl produced by Step A3 is performed to give a mixture of nitro-isomers from which the appropriate 4'-acyl-4-nitrobiphenyl is separated by a conventional process; purification of the 4'-acyl-4-nitrobiphenyl is achieved by crystallisation and column chromatography.

STEP C3: Production of 4'-n-alkyl-4-nitrobiphenyl

One example of a way of carrying out this step is as follows:

Reduction of the product of Step B3 is performed by the Huang-Minlon method giving the required 4'-n-alkyl-4-nitrobiphenyl.

EXAMPLE 4

Preparation of 4'-alkoxy-4-nitrobiphenyls by the following route:

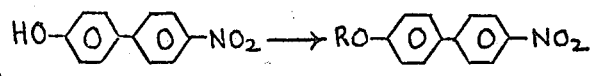

where R is an alkyl group, for example an n-alkyl group.

A conventional method is used to prepared 4'-hydroxy-4-nitrobiphenyl. This is then alkylated to give the appropriate 4'-n-alkoxy-4-nitrobiphenyl, which is purified by crystallisation and column chromatography.

EXAMPLE 5

Preparation of 7-alkyl-2-cyanofluorenes by the following route:

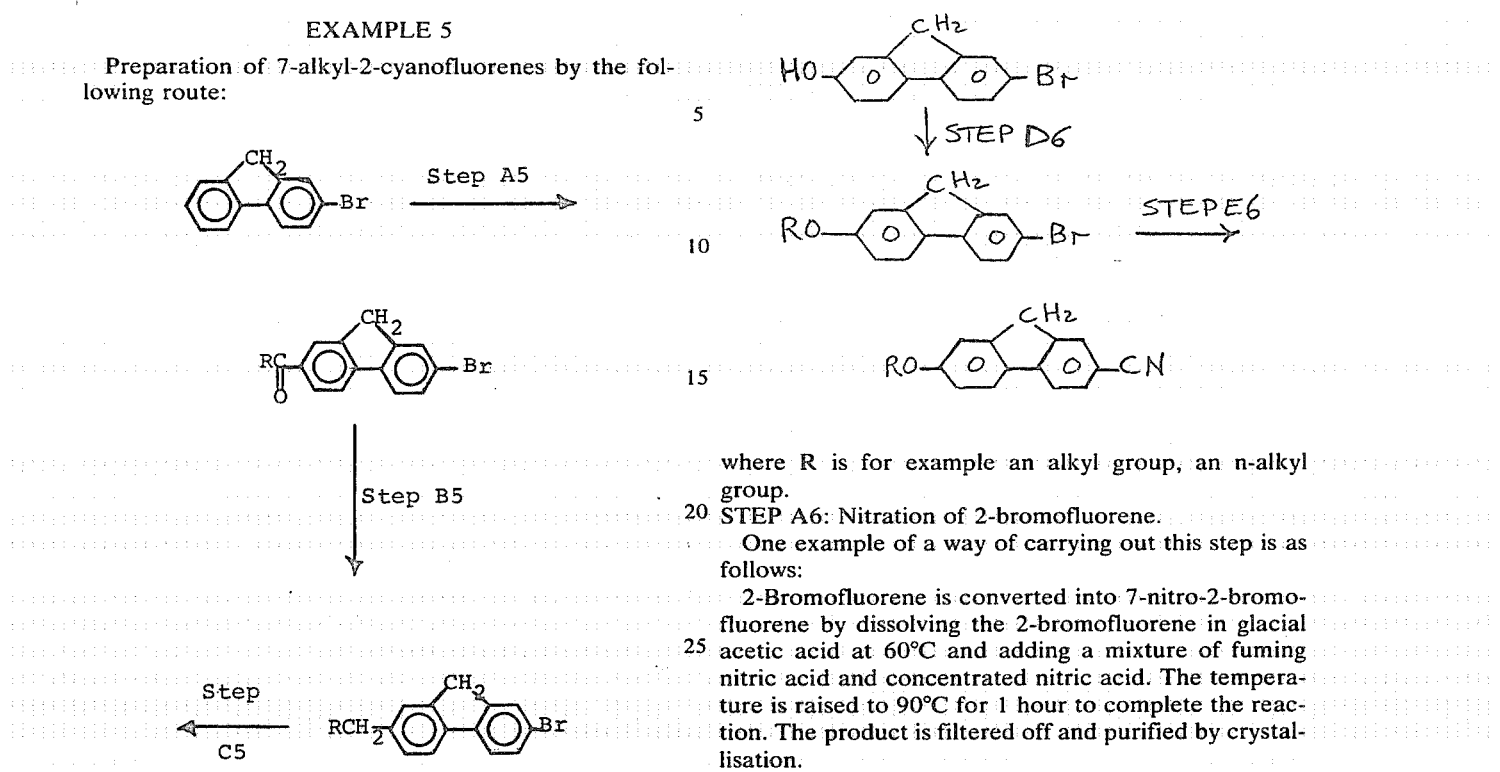

where R is an alkyl group, for example an n-alkyl group

The starting material is 2-bromofluorene which is prepared by a conventional method. Steps A5, B5 and C5, may be carried out respectively in the same way as Steps A1, B1 and C1 described in Example 1, above.

EXAMPLE 6

Preparation of 7-alkoxy-2-cyanofluorenes by the following route:

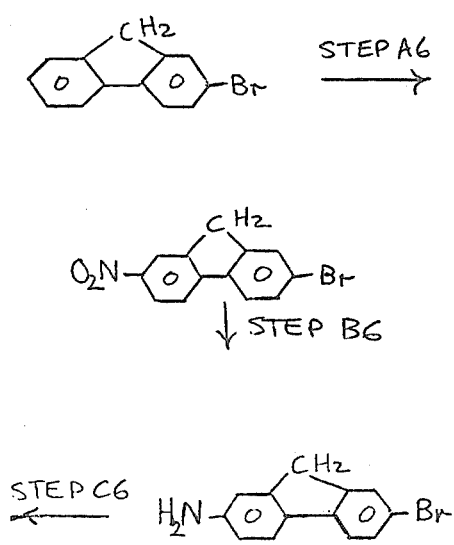

where R is for example an alkyl group, an n-alkyl group.

STEP A6: Nitration of 2-bromofluorene.

One example of a way of carrying out this step is as follows:

2-Bromofluorene is converted into 7-nitro-2-bromofluorene by dissolving the 2-bromofluorene in glacial acetic acid at 60°C and adding a mixture of fuming nitric acid and concentrated nitric acid. The temperature is raised to 90°C for 1 hour to complete the reaction. The product is filtered off and purified by crystallisation.

STEP B6: Reduction to 7-amino-2-bromofluorene.

One example of a way of carrying out this step is as follows:

The reduction of 7-nitro-2-bromofluorene produced by step A6 is achieved by dissolving the 7-nitro-2-bromofluorene in hot glacial acetic acid and adding stannous chloride dissolved in concentrated hydrochloric acid. After heating under reflux, the amine hydrochloride so produced is filtered off and digested with warm aqueous sodium hydroxide. The product is purified by crystallisation.

STEP C6: The production of 7-hydroxy-2-bromofluorene.

One example of a way of carrying out this step is as follows:

The conversion of 7-amino-2-bromofluorene produced by step B6 into 7-hydroxy-2-bromofluorene is carried out in a similar manner to that described as an example of Step C2 above.

STEP D6: The production of 7-n-alkoxy-2-bromofluorene.

One example of a way of carrying out this step is as follows:

7-hydroxy-2-bromofluorene produced by Step C6 is alkylated in the same way as described in the example of Step D2 above to give 7-n-alkoxy-2-bromofluorene.

STEP E6: The production of 7-n-alkoxy-2-cyanofluorene.

One example of a way of carrying out this step is as follows:

7-n-alkoxy-2-bromofluorene produced by Step D6 is converted into 7-n-alkoxy-2-cyanofluorene by heating in dimethylformamide with cuprous cyanide in a way similar to the particular example of Step E2 described above.

EXAMPLE 7

Preparation of a laterally methyl substituted 4'-alkoxy-4-cyanobiphenyl by the following route:

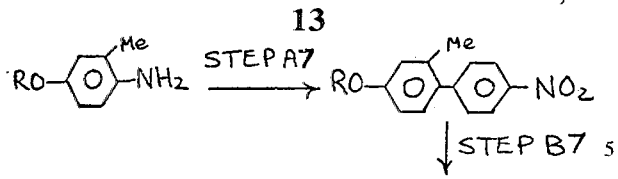

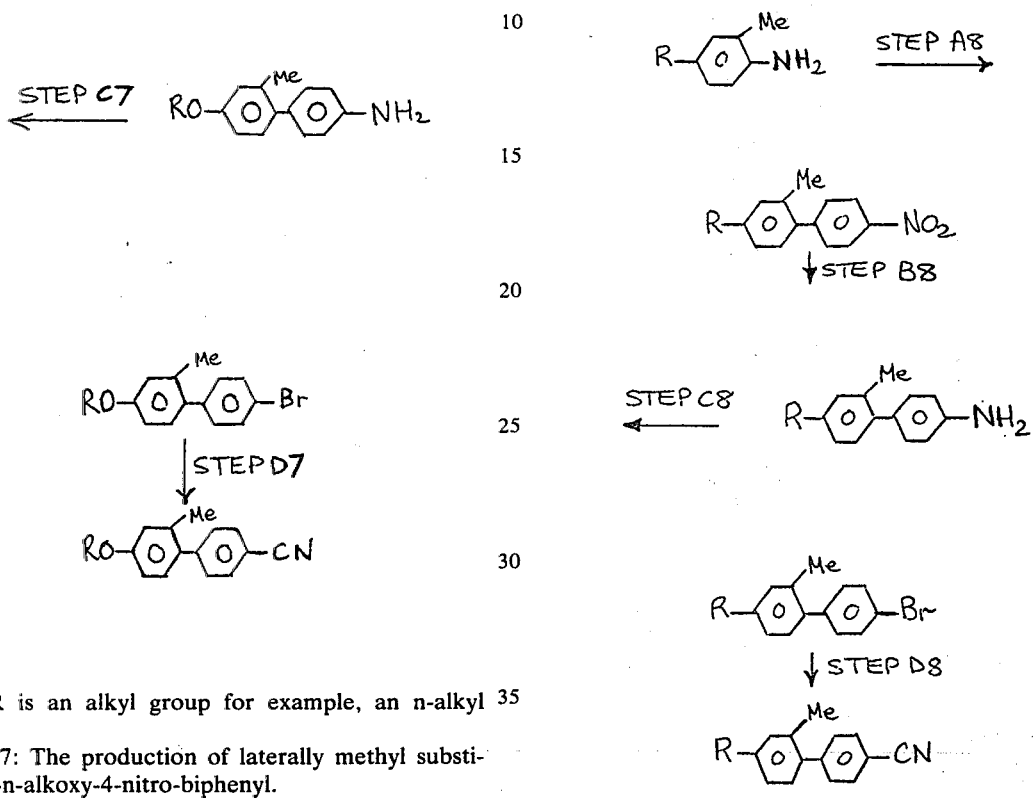

where R is an alkyl group for example, an n-alkyl group.

STEP A7: The production of laterally methyl substituted 4'-n-alkoxy-4-nitro-biphenyl.

One example of a way of carrying out this step is as follows:

The appropriate 4-n-alkoxy-2-methylaniline is converted into laterally methyl substituted 4'-n-alkoxy-4-nitrobiphenyl by the Gomberg Reaction.

STEP B7: The production of laterally methyl substituted 4'-n-alkoxy-4-aminobiphenyl.

One example of a way of carrying out this step is as follows:

The laterally methyl substituted 4'-n-alkoxy-4-nitrobiphenyl produced by step A7 is reduced by iron pin dust reduction in a similar way to the particular example of Step B2 described above to produce laterally methyl substituted 4'-n-alkoxy-4-aminobiphenyl.

STEP C7: The production of laterally substituted 4'-n-alkoxy-4-bromobiphenyl.

One example of a way of carrying out this step is as follows:

The laterally methyl substituted 4'-n-alkoxy-4-aminobiphenyl produced by Step B6 is converted into the laterally substituted 4'-n-alkoxy-4-bromobiphenyl by diazotization in a way similar to the particular example of Step C2 described above. This is followed by the addition of cuprous bromide.

STEP D7: The production of laterally methyl substituted 4'-n-alkoxy-4-cyanobiphenyl.

One example of a way of carrying out this step is as follows:

The laterally methyl substituted 4'-n-alkoxy-4-bromobiphenyl produced by Step C7 is converted into the equivalent cyano-compound by reaction with cuprous cyanide in dimethylformamide in the same way as the particular example of Step E2 described above.

EXAMPLE 8

The production of a laterally methyl substituted 4'-alkyl-4-cyanobiphenyl by the following route:

where R is an alkyl group for example, an n-alkyl group.

The starting material is 4-alkyl-2-methylaniline which is produced in a known way. Steps A8, B8, C8 and D8 may be carried out in a similar way to Steps A7, B7, C7 and D7 respectively

EXAMPLE 9

The production of a 4'-alkenyl-4-cyanobiphenyl by the following route:

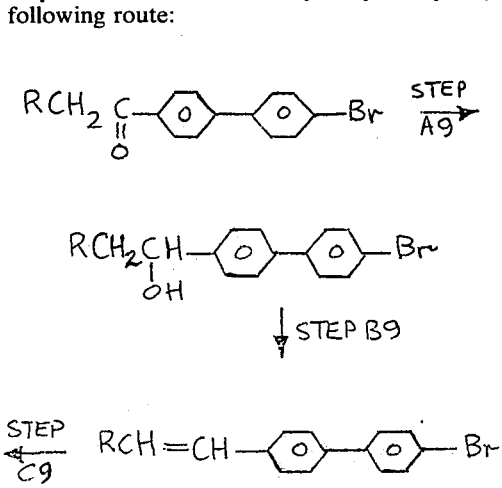

where R is an alkyl group for example, an n-alkyl group.

STEP A9: Reduction of the 4'-acyl-4-bromobiphenyl.

One example of a way of carrying out this step is as follows:

The appropriate starting ketone, prepared from 4-bromobiphenyl by acylation in the same way as the particular example of Step A1 described above. The ketone is reduced by lithium aluminium hydride in dry ether to give the appropriate alcohol which is purified by crystallisation.

STEP B9: Dehydration of the alcohol produced by Step A9.

One example of this step is as follows:

4'-alkenyl-4-bromobiphenyl is prepared by dehydration of the alcohol produced by Step A9 by heating for 10 minutes in glacial acetic acid. The product is purified by crystallisation.

STEP C9: The production of 4'-alkenyl-4-cyanobiphenyl.

One example of a way of carrying out this step is as follows:

4'-alkenyl-4-cyanobiphenyl is prepared from the bromo-compound produced by Step B9 using cuprous cyanide in dimethylformamide in the same way as Step C1 described above. The product is purified by column chromatography and distillation.

EXAMPLE 10

The production of 4'-alkoxy-4-acyloxy-biphenyl by the following route:

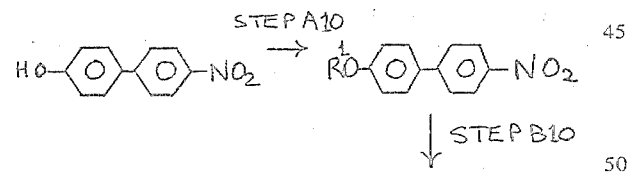

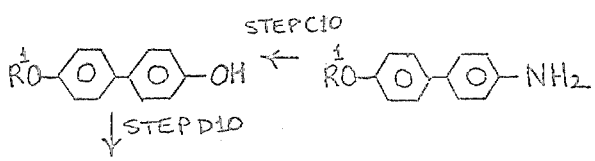

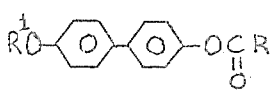

where R and R' are alkyl groups, for example n-alkyl groups.

STEP A10:
4'-n-alkoxy-4-nitrobiphenyl is produced by a conventional alkylation from 4'-hydroxy-4-nitro-biphenyl. This may be carried out in the same way as Step D2 described above.

STEP B10:
4'-n-alkoxy-4-aminobiphenyl is produced from the corresponding nitro-compound produced by Step A10 by reduction using an iron pin dust process similar to that used in the particular example of Step B2 described above.

STEP C10:
4'-n-alkoxy-4-hydroxybiphenyl is produced from the corresponding amino-compound produced by Step 10 by diazotisation and hydrolysis in a way similar to the particular example of Step C2 described above.

STEP D10:
4'-n-alkoxy-4-acyloxybiphenyl is produced from the corresponding hydroxy-compound produced by STep C10 by a conventional acylation.

EXAMPLE 11:

The production of unsymmetrical 4,4'-diacyloxybiphenyls by the following route:

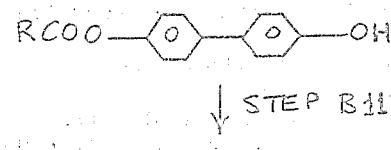

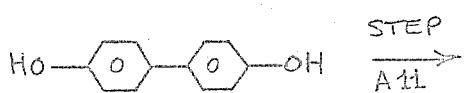

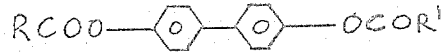

where R is an alkyl or an aryl group and R¹ is an alkyl or aryl group different from R.

STEP A11: Production of the appropriate half ester.

Commercially available 4,4'-dihydroxybiphenyl (2mol.) and the appropriate acyl chloride (RCOCl, 1 mol) are interreacted in dry pyridine and the half ester is separated from the diester and unreacted 4,4'-dihydroxybiphenyl by column chromatography and is finally crystallised.

STEP B11: Production of the unsymmetrical diester.

One example of a way of carrying out this step is as follows:

The unsymmetrical diester is prepared from the half ester (1 mol) by interaction with acryl chloride (R¹COCl, 1.1mol) in dry pyridine. The diester is purified by column chromatography and crystallisation.

EXAMPLE 12

The production of 4''-alkyl-4-cyano-p-terphenyls.

The route used is similar to that used in Example 1; however in this example the appropriate terphenyl is used in each step instead of the corresponding biphenyl used in example 1.

The starting material which is 4-bromo-p-terphenyl may be prepared by bromination of commercially available p-terphenyl by a known method.

EXAMPLE 13

The production of 4''-alkoxy-4-cyano-p-terphenyls.

The route used is similar to that used in Example 2; however, in this example the appropriate terphenyl is used in each step instead of the corresponding biphenyl used in Example 2.

The starting material which is 4''-nitro-p-terphenyl may be prepared by nitration of commercially available p-terphenyl by a known method.

EXAMPLE 14

The production of 4''-alkyl-4-nitro-p-terphenyls.

The route used is similar to that used in Example 3: however in this example the appropriate terphenyl is used in each step instead of the corresponding terphenyl used in Example 3.

The starting material which is p-terphenyl is commercially available.

EXAMPLE 15

The production of 4''-alkoxy-4-nitro-p-terphenyls.

The route used is similar to that used in Example 4, i.e. alkylation of the appropriate hydroxy compound.

The starting material which is 4'-hydroxy-4-nitro-p-terphenyl is prepared by a known method.

EXAMPLE 16

The production of di-ortho-substituted 4'-alkoxy-4-cyano-biphenyls.

The route used is similar to that used in Example 7; however in this case appropriately substituted nitrobenzene, for example, 1-methyl-2-nitrobenzene, is used as a reactant instead of the nitrobenzene used in Step A7.

EXAMPLE 17

The production of 4'-alkoxy-4-cyano-biphenyls having more than two ortho-substituents.

The route used is similar to that used in Example 7; however, in this case appropriately substituted compounds are used as starting reactants instead of the corresponding 4-n-alkoxy-2-methylaniline and nitrobenzene used in Step A7.

EXAMPLE 18

The production of 4'-alkyl-4-cyano-biphenyls having at least two orthosubstituents.

The route used is similar to that used in Example 8; however, in this case either or both of the starting reactants 4-alkyl-2-methylaniline and nitrobenzene used in Step A8 has an appropriate substituent group.

EXAMPLE 19

The production of 4'-alkyl-4-cyano-p-terphenyls having at least one ortho-substituent.

The route used is similar to that used in Examples 8 and 18; however, in this case the starting reactants are 4'-alkyl-4-aminobiphenyl prepared in a known way and nitrobenzene, at least one of which is appropriately substituted.

EXAMPLE 20

The production of 4''-alkoxy-4-cyano-p-terphenyls having at least one ortho-substituent.

The route used is similar to that used in Examples 7, 16, and 17; however, in this case the starting reactants are 4'-alkoxy-4-aminobiphenyl prepared in a known way and nitrobenzene, at least one of which is appropriately substituted.

EXAMPLE 21

The production of compounds having the formula

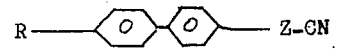

where R is an alkyl group, CN is a cyano group, and Z represents a plurality of directly para-linked benzene rings.

The route used is similar to that used in Example 1; however, in this example the appropriate multiphenyl is used in each step instead of the corresponding biphenyl used in Example 1.

EXAMPLE 22

The production of compounds having the formula

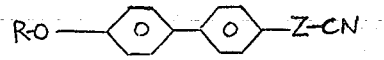

where R-O is an alkoxy group, CN is a cyano group and Z represents a plurality of directly para-linked benzene rings.

The route used is similar to that used in Example 2: however, in this example the appropriate multiphenyl is used in each step instead of the corresponding biphenyl used in Example 2.

EXAMPLE 23

The production of optically active 4'-alkoxy-4-cyanobiphenyls by the following route:

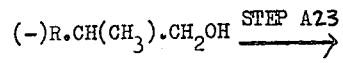

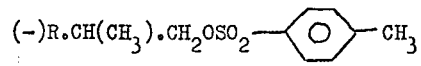

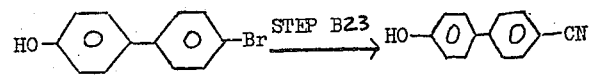

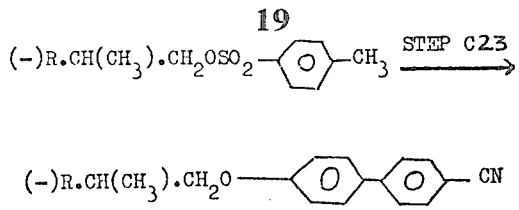

where R is an alkyl group.

One example of Steps A23, B23, and C23, particularly for the case of the compound (−) 4'-(2"-methyl-butyloxy)-4-cyano-biphenyl, is as follows:

STEP A23: The production of (−) 2-methyl-butyl-toluene-p-sulphonate.

One example of a way of carrying out this step is as follows:

To a solution of Toluene-p-sulphonyl chloride (0.094 mole) in dry pyridine (75 ml) at −5°C, (−) 2-methyl butan-1-ol (0.085 mole) is added in one portion. The solution is maintained below 0°C and stirred for 2 hours. Water (15ml) is added in portions of 1,1,1,2,5 and 5ml at 5 minute intervals, the temperature being maintained below 5°C. The solution is diluted with water (75ml). The oil so produced is extracted into chloroform and the extract washed successively with water, 2N sulphuric acid, water, 15% aqueous sodium bicarbonate and water, and finally dried over anhydrous sodium sulphate. The chloroform is removed by distillation under reduced pressure and the residual oil is distilled, the fraction being collected with a boiling point of 149°C at a pressure of 0.5mm of mercury.

STEP B23: The production of 4'-hydroxy-4-cyanobiphenyl.

One example of a way of carryiing out this step is as follows:

A mixture of 4'-hydroxy-4-bromobiphenyl (0.021mole) produced by the Steps A2, B2, and C2, of Example 2 and cuprous cyanise (0.031 mole) in dry dimethyl-formamide (75ml) are heated under reflux for 6 hours. On cooling, the reaction mixture is poured onto a stirred mixture of ferric chloride, concentrated hydrochloric acid and water. After heating at about 60°–70°C for 20 minutes the mixture is shaken with chloroform and the extract washed with 5N hydrochloric acid, water, 10% aqueous sodium bicarbonate, water and then dried. The solvent is removed and the residue is dissolved in the minimum volume of hot acetone, and the sufficient light petroleum (boiling point 40°–60°C) is added to produce a slight turbidity. The solution is refrigerated and the crystals are filtered off. The material is further purified by sublimation at a bath temperature of 160°C at 0.3mm; this yields a colourless solid.

STEP C23: The production of (−)4'-(2"-methyl-butyloxy)-4-cyanobiphenyl.

One example of a way of carrying out this step is as follows:

To 4'-hydroxy-4-cyanobiphenyl (0.01 mole), a solution of sodium (0.01 g atom) in dry ethanol (25ml) is added and the mixture stirred until complete solution is obtained. The ethanol is removed by distillation under reduced pressure. To the sodium salt of the hydroxy compound so produced is added in dry dimethylformamide (55ml) the tosylate (0.011 mole) prepared by step A23 and the mixture is heated and stirred at 110°–130°C for 7 hours. After leaving to stand overnight, the reaction mixture is poured into water (100ml) and the organic material is extracted into ether. The ethereal extract is washed successively with water, 15% aqueous sodium carbonate and water, and dried over anhydrous sodium carbonate. The ether is removed by distillation and the solild residue is purified by column chromatography on silicic acid using chloroform as the solvent.

The product eluted from the column is crystallised from ethanol and finally distilled, the fraction being collected at a bath temperature of 130° –135°C at a pressure of 0.3mm of mercury.

Other compounds embodying the invention which are ortho-substituted derivatives of

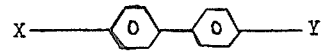

but in which the ortho-substituent(s) is (are) a halogen atom may be prepared by methods analogous to Example 7.

Other compounds embodying the invention which are derivatives of

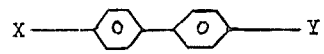

in which two of the ortho-positions are bridged by a bridging group and in which the bridging group is either

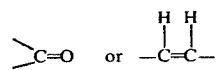

may be prepared by methods analogous to Example 6.

Other compounds embodying the invention which have more than two directly para-linked benzene rings and of which the end ring remote from the para-substituent X is substituted in the para-position by an acyloxy group may be prepared by methods analogous to Example 11.

Generally, compounds mentioned in this specification as examples in connection with the embodiments of the invention are potentially most useful when the number of carbon atoms in the para-substituent group X is 30 or less. If the compounds do not exhibit liquid crystal phases per se they may exhibit such phases when mixed with other materials such that the resultant materials constituting the mixtures exhibit liquid crystal phases.

Compounds having the formula

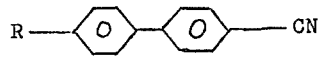

and

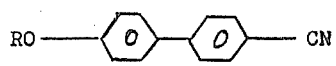

where R is an n-alkyl group, are particularly useful compounds exhibiting liquid crystal phases per se in the range where R is between 3 and 10.

Generally, compounds mentioned in this specification may have a chain of carbon atoms in their para-substituent group X which chain is either normal (straight) or branched. Generally, compounds in which the para-substituent X has a branched carbon chain are potentially useful throughout roughly the same range of numbers of carbon atoms in the parasubstituent X as those in which the para-substituent X has a normal carbon chain. However, some specific cases are given in the following table which lists examples of compounds P having specific para-substituents Y and the corresponding numbers N of carbon atoms in the para-substituent X for each of the compounds P to be potentially useful. R represents an alkyl group in each case ii. the Freedericks effect in which the direction vector of the molecules of a liquid crystal is changed from a first direction to a second direction perpendicular to the first direction by the action of an electric field applied in the second direction.

iii. the phase-change effect in which the phase of a liquid crystal may be changed between cholesteric and field-induced nematic by the action of an electric field;

| P | | N | |
|---|---|---|---|
|  R———⟨O⟩—⟨O⟩—CN, R Normal | | 3 to 24 | |
| 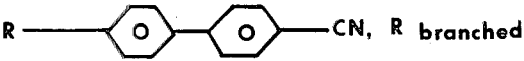 R———⟨O⟩—⟨O⟩—CN, R branched | | 3 to 30 | |
|  RO———⟨O⟩—⟨O⟩—CN, R normal | | 3 to 30 | |
| 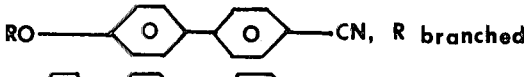 RO———⟨O⟩—⟨O⟩—CN, R branched | | 3 to 24 | |
| 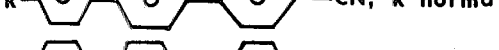 R—⟨O⟩—⟨O⟩—⟨O⟩—CN, R normal | | 2 to 24 | |
| 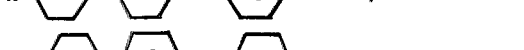 R—⟨O⟩—⟨O⟩—⟨O⟩—CN, R branched | | 3 to 24 | |
|  RO—⟨O⟩—⟨O⟩—⟨O⟩—CN, R branched | | 3 to 24 | |
| 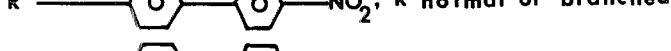 R———⟨O⟩—⟨O⟩—NO$_2$, R normal or branched | | 3 to 24 | |
| 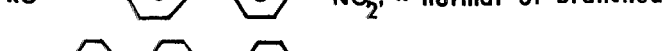 RO———⟨O⟩—⟨O⟩—NO$_2$, R normal or branched | | 3 to 24 | |
| 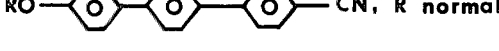 RO—⟨O⟩—⟨O⟩—⟨O⟩—CN, R normal | | 2 to 24 | |

Some nematic liquid crystal materials embodying the present invention, such as

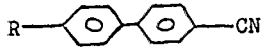

where R represents an n-alkyl group, may be produced having a positive dielectric anisotropy (difference between the dielectric constant measured parallel to the long molecular axis and the dielectric constant measured perpendicular to this axis) whilst others embodying the invention, such as

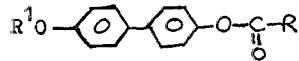

where R and R$^1$ represent n-alkyl groups, may be produced having a negative dielectric anisotropy.

Nematic liquid crystal materials having a positive dielectric anisotropy may be used in devices employing the following known effects;

i. the Schadt-Helfrich effect in which a twisted nematic liquid crystal (normally located between two transparent parallel plates such that the direction vector of the molecules is in the plane of the plates but varies over an angle of 90° from one plate to the other) located between an optical polariser and analyser exhibits an electric field dependent optical activity when an electric field is applied across the liquid crystal.

in this effect the nematic material is mixed with an optically active material to produce a chlolesteric material.

Nematic liquid crystal materials having a negative dielectric anisotropy may be used in devices employing the known dynamic scattering effect in which the molecules of the nematic liquid crystal are misorientated into a non-uniform (non-ordered) scattering state by the action of an electric current.

Similarly, some cholesteric liquid crystal materials embodying the present invention have a positive dielectric anisotropy, for example those containing a compound

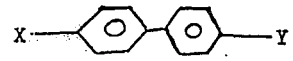

in which the parasubstituent Y is a cyano group, and others have a negative dielectric anisotropy, for example those containing a compound

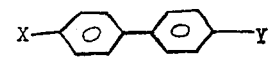

in which the para-substituent Y is an acyloxy group.

Cholesteric materials embodying the invention having a positive dielectric anisotropy may be used in the phase change effect. Cholesteric materials embodying the invention having a negative dielectric anisotropy may be used in the so-called "memory effect".

Examples of devices embodying the invention will now be described.

As an example of the use of a nematic liquid crystal material and of a cholesteric liquid crystal material embodying the present invention a phase change effect device also embodying the invention will now be described. It is known that a method of producing cholesteric liquid crystal material suitable for use in a phase change effect device involves mixing an optically active liquid crystal material with a nematic liquid crystal material or a mixture of nematic liquid crystal materials. Using that method Mixture 4 or Mixture 5 (Table 3) defined above, may be provided as the basic material for a phase change effect device.

FIG. 1 is a cross-sectional plan view, partly in circuit form, of an electro-optic liquid crystal phase change effect device embodying the invention. A thin layer 17 of Mixture 4 or Mixture 5 defined above is contained between a glass slide 19 and a glass slide 29. The glass slide 19 has on its surface in contact with the layer 17 a coating 23 of tin oxide. The glass slide 29 has on its surface in contact with the layer 17 a coating 25 of tin oxide. The glass slide 19 has a region overlapping the end of the glass slide 29 in order that an electrical connection 31 may be made to the tin oxide coating 23. Likewise, the glass slide 29 has a region overlapping the end of the glass slide 19 in order that an electrical connection 33 may be made to the tin oxide coating 25. A battery 37 may be applied between the connection 31 and the connection 33 when a switch 35 in series with the battery 37 is closed. The battery 37 is such that the electric field strength obtained therefrom across the layer 17 is greater than the critical field strength for the phase change effect. The surface of the glass slide 19 not in contact with the layer 17 contains a silver coating mirror 39. The layer 17 may be sealed between the glass slides 19 and 29 by means of a ring 41 of Araldite (trade mark) or other suitable sealing material.

A dark screen S is located at an acute angle in front of the glass slide 19 in such a position that the reflection of the screen S can be seen in the mirror 39 by an eye E as indicated in the drawing when the layer 17 is transparent.

When the switch 35 is open the image seen in the mirror 39 is bright. This is because the layer 17 is opaque and reflects ambient light into the eye E. However, when the switch 35 is closed the image seen in the mirror is dark. This is because the layer 17 has become transparent and the image of the screen S is seen in the mirror 39. When the switch 35 is opened again the image seen is again bright because the layer 17 is opaque again.

A display device based on the device described with reference to FIG. 1 may be made by forming the coatings 23 and 25 in a known way such that they are shaped in the form of localised characters or symbols. For such a display the switches connected to each character or symbol, i.e. corresponding to the switch 35, may be electronically operated by control logic (not shown).

In an alternative device the electric field applied may be alternating (at a frequency of up to about 50 kHz) instead of direct.

FIG. 2 is a schematic diagram of a liquid crystal information storage or display device of a known kind but incorporating novel material embodying the invention; the device illustrates use of either smectic or cholesteric material embodying the invention. A layer 63 of either cholesteric liquid crystal material containing the compound

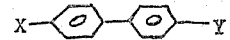

or of smectic liquid crystal material containing the compound

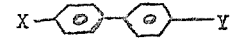

as defined above, or a derivative thereof as defined above is contained between glass slides 65, 67 having conducting coatings 69, 68 on their respective inner faces. A laser 71 producing an output beam 73 in the infrared part of the spectrum is arranged so that the beam 73 can be scanned over the slide 65 and the coating 69 by a conventional laser deflector 75. The slide 65 is transparent to the beam 73, but the coating 69 absorbs the beam 73. A voltage source 77 providing an alternating output is electrically connected to the coating 68 and to the coating 69 through a switch 70.

The device operates in the following way. Information is written by the beam 73 on the coating 69, and on the layer 63 by thermal conduction from the coating 69. The heat conducted to the layer 63 is sufficient to raise the temperature of the selected localised areas of the layer 63 and to cause the phase of those areas to change. If the material of the layer 63 is originally in the cholesteric mesophase the phase is changed to the isotropic liquid phase. If the material is originally in the smectic mesophase the phase is changed to the nematic mesophase, if the material has one, or to the isotropic liquid phase. After the beam 73 has heated a given area of the coating 69 and of the layer 63 and has been deflected to another area the given area rapidly cools again; the material in that area returns to its original phase. However, it returns to a cloudy or scattering form of the original phase. Therefore if the areas of the layer 63 not scanned by the beam 73 are in the clear or non-scattering form of the original phase the areas scanned are distinguished from those not scanned by their optical scattering properties. Therefore if the layer 63 is observed visually through the slide 67 and the coating 68, either after the beam 73 has been removed or whilst it is in operation through an appropriate filter, the information written can be seen. The coatings 69, 68 are made optically transparent for this purpose.

Erasing stored or displayed information is carried out by scanning the layer 63 with the beam 73 whilst applying an electric field across the layer 63 by closing the switch 70. The material of the layer 63 is again heated to change phase and cooled again to return to its original phase; however in this case the voltage causes the material to return to the clear form of the original phase.

Information can alteratively be erased by scanning the layer 63 with the beam 73 without using the applied electric field provided that an appropriately slow scanning rate is used for the beam 73.

FIG. 3 is a schematic diagram of a time clock or watch; the clock or watch illustrates the use of a liquid crystal display embodying the invention. A quartz crystal oscillator 81 has an oscillation frequency of 32.168 kHz. An output signal from the oscillator at that frequency is divided in a count down unit 83 providing an output signal at a frequency of 64 Hz. The output signal is applied to a logic unit 85 which further divides the frequency by sixty four. The logic unit 85 generates a single pulse every second. It counts these second pulses and provides a minute pulse every time sixty of the second pulses have been counted. It also counts the minute pulses and provides an hour pulse every time sixy of the minute pulses have been counted.

The second, minute and hour pulses are fed to operate a gate (not shown) within the logic unit 85. The gate allows operating signals to be applied via selected members in a series of conductors 86 to a liquid crystal display 87. When a second, minute or hour pulse arrives at the gate of the unit 85 it causes the selected members of the conductors 86 to be changed appropriately.

The display 87 is a 3-section digital display. A first section 88 displays the appropriate second digits, a second section 89 displays the appropriate minute digits and a third section displays the appropriate hour digits. The gate of the logic unit 85 selects the appropriate digits to be operated in the sections 88, 89, and 90 by selecting the appropriate conductors 86 for applying operating signals. When it receives a second, minute or hour pulse the gate changes the selected members of the conductors 86 to those required for the next appropriate digits in chronological sequence.

The display 87 operates in any known way; for example its digits can be operated by the phase-change effect in the way described with reference to FIG. 1. The liquid crystal material used for the display 87 is chosen to suit the method of operation. However the material which is in the nematic, cholesteric or smectic mesophase as appropriate contains at least one compound

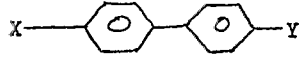

as defined above or a substituted derivative thereof.

The count down unit 83 and the logic unit 85 can respectively be CMOS SCL 5423 (or 5425) and CMOS SCL 5424 (or 5428) digit/decoder driver manufactured by Solid State Scientific Inc.

We claim:
1. A liquid crystal compound having one of the following molecular structures, the molecular structure of the compound being selected from one of the following structures: the structure

; a simple ortho-substituted derivative of the structure

wherein the substituent is selected from the group consisting methyl and halogen; and a derivative of the structure

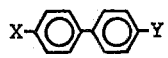

in which a simple bridging group is contained between two of the ortho-positions of said structure and said simple bridging group is selected from the group consisting of

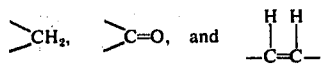

wherein X and Y are different para-substituents of the kind which promote liquid crystal behavior, the para-substituent X being a group selected from the following list: an alkoxy group having more than one carbon atom; an alkyl group; an alkanoyloxy group; and an alkenyl group; and the para-substituent Y being selected from the following list: a cyano group; a benzene ring substituted in the para-position by a cyano group; and a plurality of directly para-linked benzene rings in which the end ring remote from the substituent X is substituted in the para-position by a cyano group.

2. A material as claimed in claim 1 and wherein the para-substituent Y is a cyano group.

3. A material as claimed in claim 1 and wherein the para-substituent Y is a benzene ring substituted in the para-position by a cyano group.

4. A material as claimed in claim 1 and wherein the para-substituent Y is a plurality of directly para-linked benzene rings, the end ring remote from the para-substituent X of which is substituted in the para-position by a cyano group.

5. A material as claimed in claim 1 and wherein the para-substituent X is an alkyl group.

6. A material as claimed in claim 1 and wherein the para-substituent X is an alkoxy group having more than one carbon atom.

7. A material as claimed in claim 1 and wherein the para-substituent X is an alkanoyloxy group.

8. A material as claimed in claim 1 and wherein the para-substituent X is an alkenyl group.

9. A material as claimed in claim 1 and wherein the molecular structure of the said compound is such that the said compound has at least one of the ortho positions of the structure

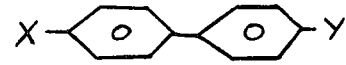

substituted with a substituent selected from the group consisting of methyl and halogen.

10. A material as claimed in claim 9 and wherein at least one of the said ortho positions is substituted with is a methyl group.

11. A material as claimed in claim 9 and wherein at least one of the said ortho positions is substituted with is a halogen atom.

12. A material as claimed in claim 1 and wherein the said compound has two of the ortho positions of the structure

substituted by a simple bridging group selected from the group consisting of

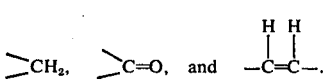

13. A material as claimed in claim 12 and wherein the said compound has the molecular structure

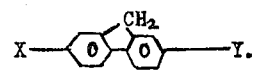

14. A material as claimed in claim 12 and wherein the said compound has the molecular structure

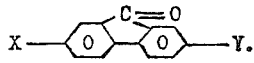

15. A material as claimed in claim 12 and wherein the said compound has the molecular structure

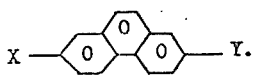

16. A material as claimed in claim 1 and wherein the para-substituent X has a chain of carbon atoms which is a normal chain such that the material exhibits a nematic or smectic mesophase.

17. A material as claimed in claim 1 and wherein the para-substituent X has a chain of carbon atoms which is a branched chain.

18. A material as claimed in claim 17 and wherein the branched chain of carbon atoms is such that the para-substituent X has an asymmetric optically active centre, such that the said material exhibits a cholesteric mesophase.

19. A material as claimed in claim 1 and wherein the para-substituent X contains at most 30 carbon atoms.

20. A material as claimed in claim 16 and wherein the said compound has the formula

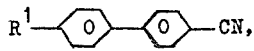

where $R^1$ is an n-alkyl group having at least 3 and at most 24 carbon atoms.

21. A material as claimed in claim 20 and wherein $R^1$ is an n-alkyl group having at least 3 and at most 10 carbon atoms.

22. A material as claimed in claim 17 and wherein the said compound has the formula

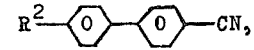

where $R^2$ is a branched alkyl group having at least 3 and at least 30 carbon atoms.

23. A material as claimed in claim 16 and wherein the said compound has the formula

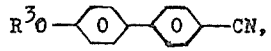

where $R^3O$ is an n-alkoxy group having at least 3 and at most 30 carbon atoms.

24. A material as claimed in claim 23 and wherein $R^3O$ is an n-alkoxy group having at least 3 and at most 10 carbon atoms.

25. A material as claimed in claim 17 and wherein the said compound has the formula

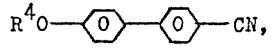

where $R^4O$ is a branched alkoxy group having at least 3 and at most 24 carbon atoms.

26. A material as claimed in claim 16 and wherein the said compound has the formula

where $R^5$ is an n-alkyl group having at least 2 and at most 24 carbon atoms.

27. A material as claimed in claim 17 and wherein the said compound has the formula

where $R^6$ is a branched alkyl group having at least 3 and at most 24 carbon atoms.

28. A material as claimed in claim 16 and wherein the said compound has the formula

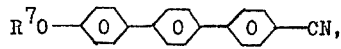

where $R^7O$ is an n-alkoxy group having at least 2 and at most 24 carbon atoms.

29. A material as claimed in claim 17 and wherein the said compound has the formula

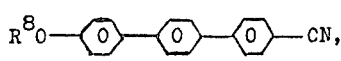

where $R^8O$ is a branched alkoxy group having at least 3 and at most 24 carbon atoms.

30. A material as claimed in claim 1 and wherein the molecular structure of the said compound is such that the said material exhibits it crystalline solid to liquid crystal transition at a temperature which is at most 30°C.

31. The liquid crystal compound of claim 1 which is

32. The liquid crystal compound of claim 1 which is

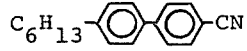

33. The liquid crystal compound of claim 1 which is

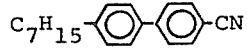

34. The liquid crystal compound of claim 1 which is

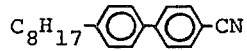

35. The liquid crystal compound of claim 1 which is

36. In a liquid crystal device including means for containing a region of liquid crystal material, a region of liquid crystal material contained in the containing means, and means for applying an external stimulus to the material to alter the molecular arrangement in the material,
the improvement which comprises using as the liquid crystal material a compound set out in claim 1.

37. A device as claimed in claim 36 and wherein the external stimulus applied by the means for applying is an electric field.

38. A device as claimed in claim 36 and wherein the external stimulus applied by the means for applying is a temperature change.

39. A device as claimed in claim 37 and wherein the containing means includes two adjacent plates at least one of which is optically transparent, the liquid crystal material being contained in the space between the plates and wherein the means for applying an electric field includes a film of conducting material forming an electrode deposited on the inner facing surfaces of the plates.

40. A device as claimed in claim 39 and wherein the plates are made of glass and the conducting films are made of tin oxide.

41. A device as claimed in claim 39 and wherein the device is an electro-optic display.

42. A device as claimed in claim 41 and wherein the electrodes have shapes therein corresponding to one or more characters or symbols.

43. A device as claimed in claim 41 and wherein the display is the indicator display of an instrument.

44. A device as claimed in claim 43 and wherein the indicator display is that of a time watch or clock.

* * * * *